United States Patent [19]

Ocello

[11] Patent Number: 5,431,952
[45] Date of Patent: Jul. 11, 1995

[54] METHOD FOR PRESERVATION OF BIOLOGICAL TISSUE

[75] Inventor: Peter J. Ocello, Charlotte, Mich.

[73] Assignee: Board of Trustees Operating Michigan State University, East Lansing, Mich.

[21] Appl. No.: 202,508

[22] Filed: Feb. 28, 1994

[51] Int. Cl.⁶ .............................................. A01N 1/00
[52] U.S. Cl. ...................... 427/4; 427/2.11; 427/296; 427/323
[58] Field of Search .......... 427/4, 2.11, 398.4, 427/289, 323, 296, 387; 436/174; 62/100, 62

[56] References Cited

U.S. PATENT DOCUMENTS

| | | |
|---|---|---|
| 2,606,843 | 8/1952 | Fessenden . |
| 2,658,836 | 11/1953 | Fessenden . |
| 2,698,809 | 1/1955 | Fessenden . |
| 3,573,082 | 3/1971 | Fremling . |
| 4,019,958 | 4/1977 | Hell et al. ............... 195/62 |
| 4,205,059 | 5/1980 | von Hagens . |
| 4,244,992 | 1/1981 | von Hagens . |
| 4,278,701 | 7/1981 | von Hagens . |
| 4,320,157 | 3/1982 | von Hagens . |
| 4,332,922 | 6/1982 | Kossmehl et al. ............... 427/2 |
| 4,510,169 | 4/1985 | Linner . |
| 4,567,847 | 2/1986 | Linner . |
| 4,742,690 | 5/1988 | Linner . |
| 4,745,771 | 5/1988 | Linner . |
| 4,784,873 | 11/1988 | Kienecker et al. . |
| 4,838,253 | 6/1989 | Brassington et al. ............... 427/2 |
| 4,839,194 | 6/1989 | Malluche et al. ............... 427/4 |
| 5,089,288 | 2/1992 | Berger . |
| 5,300,540 | 4/1994 | Masters ............... 427/4 |

OTHER PUBLICATIONS

Journal of the International Society of Plastination vol. 1, 1 to 48 (1987). no month available.
Journal of the International Society of Plastination vol. 6, 11 to 45 (1992) Jul.
von Hagens, G., J.I.S.P., 194:247–256 (1979) (no month available).
Oral Presentation (Henry, R. W.) J. Int. Soc. Plastination, vol. 6:41–44 (1992) (no month available).
Wieglein, A. H., J. Int. Soc. Plastination, vol. 7:32–35 (1993) Aug.

*Primary Examiner*—Diana L. Dudash
*Attorney, Agent, or Firm*—Ian C. McLeod

[57] ABSTRACT

A method for silicone polymer impregnation and curing in tissue to preserve the tissue. The tissue is frozen without use of an intermediary solvent and then freeze-dried using a first vacuum. The tissue is then immersed in a non-flammable degreasing solvent, particularly 1,1,1-trichloroethane to remove lipids and the like from the tissue. The tissue is then impregnated with a silicone polymer precursor and a curing agent, and then cured under a second vacuum in a chamber (23). The impregnated polymer silicone precursor is then cured in the tissue. The tissue is preferably an anatomical specimen.

28 Claims, 1 Drawing Sheet

METHOD FOR PRESERVATION OF BIOLOGICAL TISSUE

BACKGROUND OF THE INVENTION (1) Field of the Invention

The present invention relates to a method for the preservation of a biological tissue by freeze-drying and then vacuum resin impregnation using a catalyzed silicone prepolymer which is then cured to form a transparent silicone polymer, preferably a flexible polymer, in the tissue. In particular, the present invention relates to a method which uses 1,1,1-trichloroethane as the solvent for the removal of lipids or greases from the tissue and for the impregnation of the tissue with the silicone prepolymer.

(2) Description of Related Art

The education of medical students, veterinary students and allied health personnel is significantly dependent upon the use of anatomical specimens for study. Hard tissue (skeletons) comprise only one component of the specimens available for anatomical education. These are common and environmentally safe. Skeletal material, however, constitutes only a small portion of the overall body of knowledge necessary for anatomical competency. The significant need for safe and inexpensively preserved soft tissue material remains.

Anatomical models, though readily available and safe, do not account for biological variability. This problem is faced most critically in veterinary and veterinary technology programs, biology course, public nature education and educational efforts by state and federal agencies. Traditional anatomical tissues have biohazard risks associated with the preservation and maintenance process. Potential health risks exist for students, faculty and staff with hypersensitivities and allergies to the formalin preparations used for tissue preservation. Further, the increasing number of women of reproductive years in professional programs who are exposed to these potentially hazardous materials is an additional cause for concern.

The prior art has described numerous methods for preserving biological tissue. An early method was to coat chemically preserved tissues as described in U.S. Pat. Nos. 2,606,843, 2,658,836 and 2,698,809 to Fessenden. U.S. Pat. No. 3,573,082 to Fremling and 4,784,873 to Kienecker describe various preservatives. U.S. Pat. No. 5,089,288 to Berger describes paraffin impregnation of tissue. The paraffin impregnated tissue does not provide ease of handling, since it is relatively soft and easily damaged.

U.S. Pat. Nos. 4,205,059, 4,244,992, 4,278,701 and 4,320,157 to von Hagens describe a process, referred to as "plastination" wherein a water-bearing tissue is treated with an organic solvent to remove water from the tissue. The solvent is then removed using a vacuum in the presence of a fluid precursor to a resin which replaces the solvent. Excess precursor resin is removed from the tissue and the resin is cured. The preferred resins disclosed are transparent silicone polymers. The problem is that the commercial method uses acetone as the solvent for the method which is flammable and poses a health risk. The process is slow, expensive and requires an explosion-proof laboratory. The Journal of the International Society of Plastination 1, 1 to 48 (1987) and 6 11 to 45 (1992) describe the plastination process in detail. There is a need for a method which is less hazardous.

The first three (3) of von Hagens' patents suggest direct plastination of freeze-dried tissue which was not degreased prior to the plastination step (see Column 3, lines 44 to 48). The presence of lipids or grease in the tissue is not compatible with preservation of the tissue. The cells of the embalmed tissue would collapse if the solvent was removed in the von Hagens method.

U.S. Pat. Nos. 4,567,847, 4,742,690, 4,745,771 and 4,510,169 to Linner describe a method for resin impregnation of tissue wherein cryogenic temperatures are less than $-140°$ C. and very high vacuum are used to dehydrate the tissue by freeze-drying. The equipment required for such dehydration is complicated and thus expensive; however, the problem of ice crystals fracturing the sample are said to be solved by this method. It would be an improvement if a method could be developed which avoided the temperatures and resulting equipment costs associated with this method.

OBJECTS

It is therefore an object of the present invention to provide a method which uses freeze-drying of the tissue which is rapid and safe. Further, it is an object of the present invention to provide a method which is simple and economical to perform. These and other objects will become increasingly apparent by reference to the following description and the drawing.

DESCRIPTION OF PREFERRED EMBODIMENTS

Figure 1:
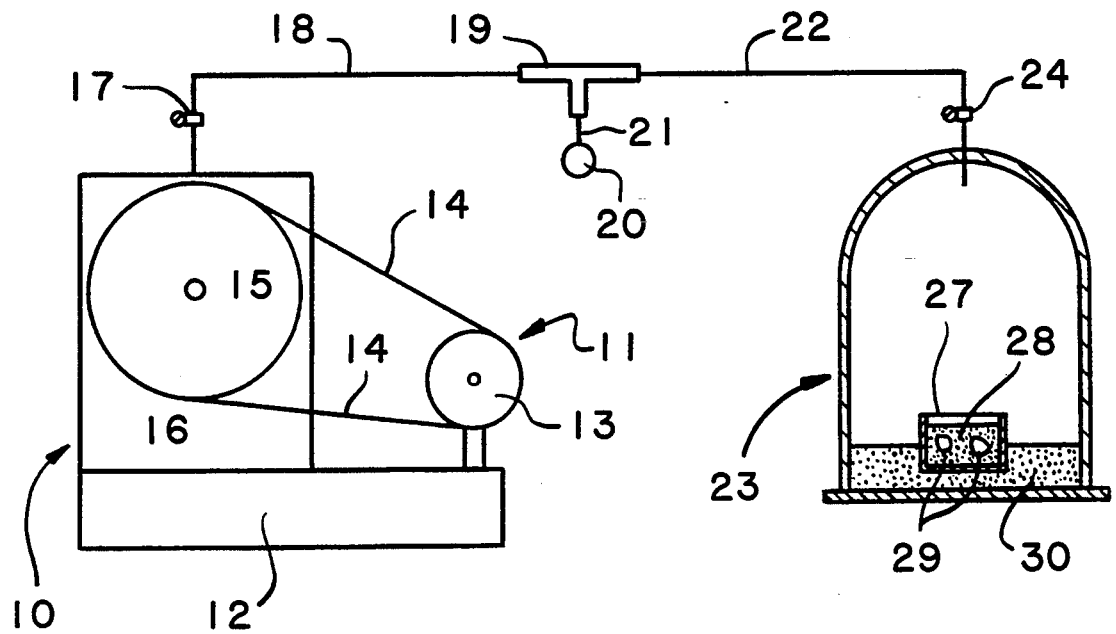
FIG. 1 is a schematic view of the apparatus used in the method of the present invention, particularly including a vacuum system 10 and a bell jar vacuum chamber 23 containing the tissue 29 to be preserved for impregnation with the silicone 28 in a flask 27.

The present invention relates to a method for preparing a preserved biological tissue which comprises: freezing a biological tissue containing water; providing a first vacuum in a chamber containing a support means for the frozen tissue to remove the frozen water from the tissue and to provide a freeze-dried tissue; immersing the freeze-dried tissue in a non-flammable degreasing solvent to remove lipids from the tissue and to impregnate the tissue with the solvent and then removing the tissue from the solvent; impregnating the freeze-dried tissue in a container with a silicone polymer precursor and a curing agent for curing the silicone polymer precursor by providing a second vacuum in a chamber containing the container, wherein the silicone polymer precursor and impregnate the specimen and the solvent is removed from the tissue to provide an impregnated tissue; and curing the polymer precursor with the curing agent to form a transparent cured silicone polymer and thus provide the preserved biological tissue.

The present invention also relates to a method for preparing a preserved biological tissue which comprises: freezing a biological tissue containing water; providing a first vacuum in a chamber containing a first support means for the frozen tissue to remove the frozen water from the tissue and to provide a freeze-dried tissue; immersing the freeze-dried tissue in a 1,1,1-trichloroethane to remove lipids from the tissue and to impregnate the tissue with the 1,1,1-trichloroethane and then removing the tissue from the 1,1,1-trichloroethane; impregnating the freeze-dried tissue in a container containing a mixture of a silicone polymer precursor and a curing agent for curing the silicone polymer precursor by providing a second vacuum in a chamber containing the container, wherein the silicone polymer precursor and impregnate the specimen and the 1,1,1-trichloroethane is removed from the tissue to provide an impregnated tissue; and curing the polymer precursor with the curing agent to form a transparent cured silicone polymer and thus provide the preserved biological tissue.

The tissue is preferably soaked in an aqueous solution of an alkali metal salt or alkaline earth metal salt, particularly a halide salt. Such salts include potassium chloride and sodium chloride. Sodium chloride is preferred. The solution preferably contains about 0.9 gram per liter of the salt by weight. The tissue can also be preserved with a commercial formalin composition. The formalin should be neutralized with a base, such as with an ammoniacal solution or preferably sodium hydroxide or other alkali metal or alkaline earth metal base, to prevent possible damage to seals in the vacuum pump. The by-product of the ammonium solution reaction with formaldehyde can interfere with curing and thus is not preferred. The tissue treated by either method is then rinsed in water, preferably for 24 to 48 hours. If necessary, in order to prevent large ice crystal formation during freezing which can damage the tissue, the tissue can be impregnated with a freezing preservation agent such as polyethylene glycol, polyether diglyme or a 15 to 20% hypertonic sucrose solution. Such freezing preservation agents are well known to those skilled in the art.

The tissue is frozen, preferably at between about 0° F. to −25° F. (−17.8° to −31.7° C.). The freeze drying is then performed using a high vacuum in a chamber containing a support means for the tissue. Preferably the vacuum is between about 20 inches of mercury or 0.94 atmosphere.

The solvent used to remove lipids and the like from the freeze dried tissue is 1,1,1-trichloroethane which is a dry-cleaning solvent and relatively nontoxic. This solvent is very effective in removing the lipids. The tissue is preferably soaked in the 1,1,1-trichloroethane for about one (1) day to one (1) week, preferably 48 to 120 hours at room temperatures between about 68° to 73° F. (20° to 23° C.). This solvent has a strong affinity for lipids and is a degreasing agent. The freeze dried tissue is much easier to degrease than the fresh tissue.

The tissue is then immersed in a silicone resin precursor with a vinyl catalyst mixed with the 1,1,1-trichloroethane and a vacuum is provided in the chamber containing a container which is used to impregnate the tissue with the precursor while removing the 1,1,1-trichloroethane from the tissue. The 1,1,1-trichloroethane is also used to dilute the resin precursor to a thinner viscosity. Usually between about 1 and 90% and preferably 15% by weight of solvent is used to provide a suitable viscosity. The vacuum is preferably between about 20 inches of mercury or 0.94 atmosphere and usually the vacuum is cycled to remove air from the chamber between no vacuum and the ultimate vacuum. The vacuum is preferably maintained in the chamber for 1 to 7 days preferably at a temperature between about 0° and 10° C. (32° F.–50° F.), preferably 3.3° C. (38° F.). These low temperatures retard the polymerization of the silicone prepolymer in the container which does not impregnate the tissue so that it can be reused.

The preferred prepolymer is a polydimethylsiloxane which is dimethyl vinyl terminated. The cured polymer is a transparent silicone polymer, particularly a dimethyl siloxane polymer. The preferred polymer is Silastic MDX4-4210 which is a divinyl dimethylpolysiloxane (Dow-Corning, Midland, Mich.) Medical Grade. Preferably the polymer is cured in the tissue outside of the chamber at room temperatures between about 68° to 73° F. (20° to 23° C.) with the curing agent to provide the cured resin impregnated tissue. The curing agent for the silicone prepolymer can be hydrogen peroxide or platinum which is used for medical grade silicones.

Anhydrous calcium sulfate or another drying agent such as silica gel, is preferably included in the vacuum chamber around the container for the silicone prepolymer to remove residual water produced from the tissue during the resin impregnation and curing step. This is important in preventing moisture from contaminating the sample.

The preserved tissue is then preferably wiped and then cured on a non-stick surface, preferably a polyethylene film until it is fully cured. The result is a perfectly preserved tissue.

The preferred tissues are anatomical tissues of various animals, particularly humans. Lower organisms can also be preserved as well as plants.

FIG. 1 shows the apparatus used in the present invention for resin impregnation including vacuum system 10 and vacuum chamber 23 containing the tissue 25 to be freeze dried mounted on a support 26 to be preserved. The system 10 includes a motor 11 mounted on a support 12. The motor 11 has a first pulley wheel 13 supporting a pulley 14 connected to a second pulley wheel 15 on a standard oil type vacuum pump 16 (having a 3 quart (2.82 liters) oil reservoir) mounted on support 12. A clamp 17 is provided on pump 16 securing hose 18 to pump 16 (preferably 1 inch OD (2.54 cm)) and ⅜ inch ID (0.375 cm). The hose 18 is connected to a "T" 19 connected to a vacuum gauge 20 by means of a hose 21 (preferably ⅝" OD (1.59 cm) and ¼ ID (0.32 cm)). A second hose 22 (like hose 18) is connected to the vacuum chamber 23, preferably a glass bell jar, by means of a clamp 24. Inside the chamber 23 is a flask 25 containing silicone 28 and tissues 29 to be preserved 27. The flask 27 is mounted on a bed 30 of anhydrous calcium sulfite as a dehydrating agent. In operation, the vacuum system 10 is operated to provide a vacuum in chamber 23. In the impregnation step, the silicone 28 (containing the 1,1,1-trichloroethane) impregnates the tissue 29. The vacuum system removes the 1,1,1-trichloroethane. The bed 30 absorbs any water produced in the chamber 23 during the impregnation. The tissue 29 is then removed from the chamber 23.

Figure 2:
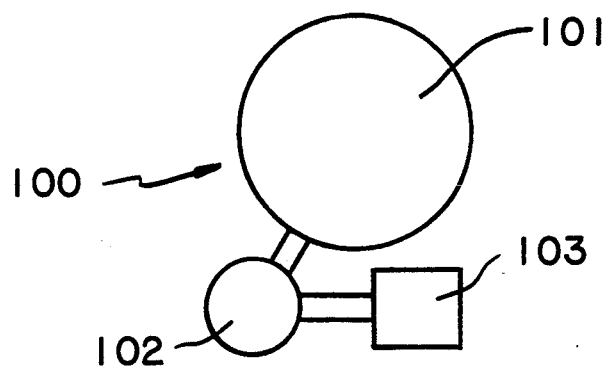
FIG. 2 is a schematic view of a standard lyophilizer 100.

FIG. 2 shows standard freeze-drying equipment including a chamber 101, a liquid condenser 102 and a vacuum pump 103. The water removed is condensed by the condenser 102.

EXAMPLE 1

The preferred steps in the method were:

| I. Tissue Preparation | |
|---|---|
| Fresh Tissue or | Fixed Tissue (embalming fluid) |
| 1. Saline Washed- | 1. Neutralized |

-continued

| | |
|---|---|
| 0.9 gram per liter for 1 to 2 hrs. depending upon the size of tissues; | tissue in 2% by weight ammonium hydroxide for 24 to 48 hours; |
| 2. | Rinsed tissue 27 in H₂O for 24 to 48 hours; |
| 3. | Frozen at −25° F. (−31.7° C.); |
| 4. | Sectioned tissue on band saw at room temperature (where necessary); |
| 5. | Freeze-dried tissue at −25° F. (−31.7° C.) and 0.94 atmosphere in a standard lyophilizer 100 (Northstar Model 3666, Nisswa, Minnesota); and |
| 6. | Degreased tissue in 1,1,1 Trichloroethane for 48 hours and air dried at room temperatures to remove 1,1,1-trichloroethane from the tissue. |
| II. Tissue Impregnation | |
| 1. | In a glass or polyethylene container or flask 27 were mixed thoroughly (by wt.): 1 lb (454 g) Silastic MDX4-4210 Dow Corning, Midland, Michigan silicone elastomer precursor, 2 oz (62 g) of curing agent and 300 ml of 1,1,1 Trichloroethane; |
| 2. | The freeze-dry section was immersed in silicone elastomer; |
| 3. | The container 27 was placed in the chamber 23 with 1 lb (454 grams) of anhydrous CaSO₄; |
| 4. | The chamber 23 was evacuated with a vacuum of about 28" of Hg (0.94 atmosphere) for approximately 30 minutes. The vacuum was released several times to dislodge air bubbles; |
| 5. | The vacuum was reinstated and the chamber 23 was placed in refrigerator for approximately 4 days at 38° F. (3.3° C.). The vacuum was checked periodically; and |
| 6. | The tissue was removed from the chamber 23 and the catalyzed prepolymer was cured at 23° C. (73° F.) for approximately 24 hours. The tissue was wiped and placed on a polyethylene or plastic film which collected and elastomer seepage. |

EXAMPLE 2

As in Example 1, a human arm taken from a cadaver fixed with a 6% glutaraldehyde/formaldehyde commercial mixture was frozen in a commercial freezer at −25° F. (−31.7° C.) and then sectioned at a thickness of 2.54 cm (1 inch). The fixed tissue had been neutralized using a weak ammonium hydroxide solution for 24 to 48 hours and then rinsed in water for same period prior to freezing. Dehydration was carried out using a commercial freeze dryer (Northstar model 3666, Nisswa, Minn.) at a temperature of −25° F. (−31.7° C.). Following complete dehydration, the specimen was submerged in 1,1,1-trichloroethane for 48 hours to remove lipids and then air dried. The section was then submerged in catalyzed Silastic MDX4-4210 elastomer precursor thinned with 1,1,1-trichloroethane as in Example 1. The specimen was placed in a chamber 23 with 1 lb (454 grams) of anhydrous CaSO₄ as in Example 1. The air in the chamber 23 was evacuated and the vacuum was released periodically to dislodge air bubbles. The evacuated chamber 23 was then placed in the refrigerator for approximately 4 days at 38° F. (3.3° C.). The specimen was removed from the chamber and cured at 73° F. (22.78° C.) for approximately 24 hours in a polyethylene film to prevent elastomer from oozing from the tissue. The impregnated tissue was flexible, resilient and transparent. After allowing time for the silicone to fully cure (about three (3) days), the tissue was sliced using a knife. Visual observation indicated that the infiltration of silicone polymer into the tissue 27 was complete.

EXAMPLE 3

A canine eye, cut sagittally, was fixed using a 10% solution of formalin. Neutralization, dehydration and impregnation has been carried out as described in Example 1. The eye was flexible, resilient and transparent.

EXAMPLES 4, 5 and 6

A second cross section through a human arm (preserved) with the same thickness as in Example 2, a raccoon brain (fresh) consisting of one hemisphere and a red rose (fresh) were prepared using the method of Example 1, except that silicone elastomer precursor was not diluted in the solvent. After the silicone was allowed to cure, the brain and human arm tissues were cut with a knife. Visual observation indicated that there was incomplete infiltration into the human tissues. It is believed that the ammonium hydroxide neutralizer interfered with the curing. The tissues were not flexible, however, they were transparent. Thus, it is important to use the solvent with the silicone precursor or to use a less viscous silicone precursor.

EXAMPLE 7

Four sagittal sections of animal eyes (tissue fixed by various standard histologic fixatives and washed in water) as the tissue were placed in 300 ml of a solution of 1,1,1-trichloroethane at room temperature under a fume hood to degrease the eyes which had been freeze dried as in Example 1. The animal eyes were air dried for less than one (1) hour to remove 1,1,1-trichloroethane in the tissue. One (1) part by weight of hardener to 10 parts by weight silicone along with 300 ml of 1,1,1-trichloroethane were mixed and the animal eyes were placed in the flask 27. The tissues were maintained in a vacuum of 28 inches of Hg (0.94 atm) overnight at room temperature 73° F. (22.78° C.). The eyes were removed from the silicone under a fume hood and allowed to cure at room temperature on a non-stick surface. The eyes were flexible and completely impregnated.

The method of the present invention produces anatomical educational materials which have not been previously available at a reasonable cost. The method is environmentally safe, inexpensive and produces educationally unique specimens. In addition, this method allows teaching universities to maintain and expand their present inventory of teaching and research specimens. Of particular importance is the applicability of this method and its products to communication and educational linkage within biomedical units, other biomedical educational institutions nationwide, and a myriad of federal and state government biological agencies, nature centers, zoos and museums.

Other non-flammable degreasing solvents could be used. The one which is particularly safe and effective is 1,1,1-trichloroethane.

It is intended that the foregoing description be only illustrative of the present invention and that the present invention be limited only by the hereinafter appended claims.

I claim:
1. A method for preparing a preserved biological tissue which comprises:
   (a) treating a biological tissue containing water with an aqueous solution consisting essentially of a com- pound selected from the group consisting of an alkali metal salt, an alkaline earth metal salt, a base and mixtures thereof and then rinsing the biological tissue with water;

(b) freezing the treated biological tissue containing water without use of an intermediary solvent, then;

(c) providing a first vacuum in a chamber containing a support means for the frozen tissue to remove the frozen water from the tissue and to provide a freeze-dried tissue;

(d) immersing the freeze-dried tissue in a non-flammable degreasing solvent to remove lipids from the tissue and to impregnate the tissue with the solvent and then removing the tissue from the solvent;

(e) impregnating the freeze-dried tissue in a container with a silicone polymer precursor and a curing agent for curing the silicone polymer precursor by providing a second vacuum in a chamber containing the container, wherein the silicone polymer precursor and the curing agent impregnate the specimen and the solvent is removed from the tissue to provide an impregnated tissue; and (f) curing the polymer precursor with the curing agent in the impregnated tissue to form a transparent cured silicone polymer and thus provide the preserved biological tissue.

2. A method for preparing a preserved biological tissue which comprises:

(a) treating a biological tissue with an aqueous solution consisting essentially of a compound selected from the group consisting of an alkali metal salt, an alkaline earth metal salt, a base and mixtures thereof and then rinsing the biological tissue with water;

(b) freezing a biological tissue containing water without use of an intermediary solvent, then;

(c) providing a first vacuum in a chamber containing a support means for the frozen tissue to remove the frozen water from the tissue and to provide a freeze-dried tissue;

(d) immersing the freeze-dried tissue in 1,1,1-trichloroethane to remove lipids from the tissue and to impregnate the tissue with the 1,1,1-trichloroethane and then removing the tissue from the 1,1,1-trichloroethane;

(e) impregnating the freeze-dried tissue in a container with a silicone polymer precursor and a curing agent for curing the silicone polymer precursor by providing a second vacuum in a chamber containing the container, wherein the silicone polymer precursor and impregnate the specimen and the 1,1,1-trichloroethane is removed from the tissue to provide an impregnated tissue; and (f) curing the polymer precursor with the curing agent to form a transparent cured silicone polymer and thus provide the preserved biological tissue.

3. The method of claim 2 wherein in step (d) the freeze-dried tissue is immersed for between about 1 day to 1 week in the 1,1,1-trichloroethane.

4. The method of any one of claims 2 or 3 wherein the first vacuum in step (c) and the second vacuum in step (e) is about 28 inches of mercury.

5. The method of claim 2 wherein the curing agent in step (e) is a platinum compound.

6. The method of claim 2 wherein the silicone polymer in step (e) is a polydimethyl siloxane.

7. The method of claim 2 wherein the preserved biological tissue is placed on a transparent film after step (f) for additional curing.

8. The method of claim 2 wherein in step (a) the tissue is washed with an aqeuous solution of sodium chloride as the compound.

9. The method of claim 2 wherein a desiccator composition is provided in the second container in step (e) to remove water which is volatilized from the tissue by the second vacuum.

10. The method of claim 9 wherein the desiccator composition is anhydrous calcium sulfate.

11. The method of claim 2 wherein in step (b) the frozen tissue is sectioned.

12. The method of claim 2 wherein the tissue in step (b) is frozen at $-17.8°$ to $-31.7°$ C. and water is removed at 28 inches of mercury in step (c).

13. The method of claim 2 wherein the second vacuum in step (e) is cycled at least once between no vacuum and the second vacuum to remove any air entrapped in the tissue or silicone polymer precursor.

14. The method of claim 13 wherein the vacuum is maintained for between about 1 to 7 days at a temperature of $0°$ to $10°$ C. after being cycled.

15. The method of claim 14 wherein the temperature is about $3.3°$ C.

16. The method of claim 2 wherein the curing agent is a divinyl polymethylsiloxane curing catalyst.

17. The method of claim 16 wherein the silicone polymer prepolymer is divinyl polydimethylsiloxane and wherein the catalyst is a platinum catalyst.

18. The method of claim 2 wherein the preserved biological tissue is flexible.

19. The method of claim 2 wherein the freeze dried tissue is dried by removing 1,1,1-trichloroethane after step (d).

20. The method of claim 2 wherein the tissue is dried after step (d) in air at room temperatures prior to impregnating the tissue.

21. A method for preparing a preserved biological tissue which comprises:

(a) freezing a biological tissue containing water without using an intermediary solvent, then;

(b) providing a first vacuum in a chamber containing a support means for the frozen tissue to remove the frozen water from the tissue and to provide a freeze-dried tissue;

(c) immersing the freeze-dried tissue in 1,1,1-trichloroethane to remove lipids from the tissue and to impregnate the tissue with the 1,1,1-trichloroethane and then removing the tissue from the 1,1,1-trichloroethane;

(d) impregnating the freeze-dried tissue in a container with a silicone polymer precursor and a curing agent for curing the silicone polymer precursor by providing a second vacuum in a chamber containing the container, wherein the silicone polymer precursor and the curing agent impregnate the specimen and the 1,1,1-trichloroethane is removed from the tissue to provide an impregnated tissue wherein the vacuum is cycled at least once to remove any air entrapped in the tissue or the silicone polymer precursor; and (e) curing the polymer precursor with the curing agent to form a transparent cured silicone polymer and thus provide the preserved biological tissue.

22. The method of claim 21 wherein the second vacuum in step (d) is cycled at least once between no vacuum and the second vacuum to remove any air entrapped in the tissue or silicone polymer precursor.

23. The method of claim 22 wherein the vacuum is maintained for between about 1 to 7 days at a temperature of 0° to 10° C. after being cycled.

24. The method of claim 23 wherein the temperature is about 3.3° C.

25. The method of claim 21 wherein the curing agent is a divinyl polymethylsiloxane curing catalyst.

26. The method of claim 21 wherein the silicone polymer prepolymer is divinyl polydimethylsiloxane and wherein the catalyst is a platinum catalyst.

27. The method of claim 21 wherein the tissue in step (a) is frozen at −17.8 to −31.7° C. and water is removed at 28 inches of mercury in step (b).

28. The method of claim 21 wherein in step (b) the frozen tissue is sectioned.

* * * * *